United States Patent [19]

Gibson

[11] Patent Number: 5,015,470

[45] Date of Patent: May 14, 1991

[54] COSMETIC COMPOSITION

[76] Inventor: Walter T. Gibson, 8 Braid Court, Wellingborough, Northants NN8 3PF, England

[21] Appl. No.: 134,422

[22] Filed: Dec. 17, 1987

[30] Foreign Application Priority Data

Dec. 23, 1986 [GB] United Kingdom ............... 8630721

[51] Int. Cl.$^5$ ............................................... A61K 7/06
[52] U.S. Cl. ............................................ 424/70; 514/2; 424/603; 424/660; 424/673; 424/663; 424/709; 424/711; 435/200
[58] Field of Search ............... 424/70, 603, 660, 673, 424/663, 709, 711; 514/880, 881; 435/200

[56] References Cited

U.S. PATENT DOCUMENTS

| | | | |
|---|---|---|---|
| 4,139,619 | 2/1979 | Chidsey, III | 424/45 |
| 4,508,707 | 4/1985 | Ayukawa | 424/70 |
| 4,529,587 | 7/1985 | Green | 424/70 |
| 4,761,401 | 8/1988 | Couchman et al. | 514/880 |

FOREIGN PATENT DOCUMENTS

| | | |
|---|---|---|
| 035919 | 9/1981 | European Pat. Off. |
| 129197 | 12/1984 | European Pat. Off. |
| 2438534 | 2/1976 | Fed. Rep. of Germany |
| 2619100 | 11/1977 | Fed. Rep. of Germany |
| 59-186991 | 10/1984 | Japan |
| 59-212424 | 12/1984 | Japan |
| 61-7209 | 1/1986 | Japan |
| 8504577 | 10/1985 | PCT Int'l Appl. |

OTHER PUBLICATIONS

Effect of Acid Mucopolysaccharides on Hair Growth in the Rabbit (Meyer, Kaplan & Steigleder), Proceedings of the Society of Experimental & Biological Sciences, vol. 108, pp. 59–61.

Advances in Enzymology, Edited by Alton Meister, Inerscience Publisher, Div. of John Wiley & Sons (vol. 36—1972).

Primary Examiner—Ronald W. Griffin
Attorney, Agent, or Firm—Melvin H. Kurtz

[57] ABSTRACT

A composition suitable for topical application to mammalian skin or hair for inducing, maintaining or increasing hair growth comprises:
(i) a first chemical inhibitor chosen from proteoglycanase inhibitors, glycosaminoglycanase inhibitors, glycosaminoglycan chain cellular uptake inhibitors or mixtures thereof; and
(ii) a cosmetically acceptable vehicle for the chemical inhibitor;

provided that when the first chemical inhibitor is a weak inhibitor, such that a 1 mM aqueous solution of the inhibitor reduces proteoglycanase activity, glycosaminoglycanase activity or cellular uptake of glycosaminoglycan chains, by from 5 to 50%, in accordance with at least one of the assay tests as herein described, then there is also present in the composition a second chemical inhibitor and/or an activity enhancer. When minoxidil is the sole chemical inhibitor, then the activity enhancer is a penetration enhancer chosen from a limited number of materials, including certain esters and cationic polymers.

The total amount of chemical inhibitor present in the composition is sufficient to increase hair growth in the rat, when said composition is applied topically thereto, by at least 10% more than that obtainable using a control composition from which the said inhibitors have been omitted.

31 Claims, No Drawings

COSMETIC COMPOSITION

FIELD OF THE INVENTION

The invention relates to cosmetic and pharmaceutical compositions for topical application to mammalian skin or hair, containing an enzyme inhibitor which is capable of promoting hair growth, especially terminal hair growth on the human scalp.

BACKGROUND

The Hair Growth Cycle

It should be explained that in most mammals, hair does not grow continuously, but undergoes a cycle of activity involving alternate periods of growth and rest. The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen, which is heralded by the cessation of mitosis, and during which the follicle regresses upwards through the dermis and hair growth ceases, (iii) the resting stage known as telogen, in which the regressed follicle contains a small secondary germ with an underlying ball of tightly packed dermal papilla cells.

The initiation of a new anagen phase is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth by the topical application of hair tonics and the like, with the possible exception of minoxidil, none has been shown to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is by transplantation of hair to the bald areas. This is, however, an extremely painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question comprises a pyrimidine carbamate.

It has also been reported in US patent no. 4 139 619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth reported independently by Bazzano and Chidsey, following topical application of minoxidil or related compounds, there is general concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity. There is also evidence that certain side effects have been experienced following topical application of minoxidil.

In addition to the alleged benefits of employing the pyrimidine carbamates of Bazzano or minoxidil of Upjohn, many other hair regrowth studies have been reported in the literature. In particular, the work of Meyer et al (1961) in the Proceedings of the Society of Experimental and Biological Medicine, 108, 59–61, is worthy of mention. Meyer and his co-workers repeatedly injected acid mucopolysaccharides into the skin of shaved rabbits and reported observing the initiation of the hair growth cycle with stimulation of hair growth which in some instances appeared to be thicker than usual. They found that heparan sulphate was particularly active, while dermatan sulphate and chondroitin-6-sulphate were also active in this respect, but to a lesser extent.

It has also been reported by Frajdenrajch in EP-A-0 035 919 to include chondroitin sulphate in a hair composition in order to prevent loss and encourage growth of the hair.

Also, Shansho Seigaku in JA-59/186911 describes a shampoo containing a mucopolysaccharide such as chondroitin sulphate.

There are also other references, mainly of Japanese origin, which claim the use of chondroitin sulphate in preparations for topical application to human skin, particularly as hair tonics.

Kohler in DE OLS 24 38 534 reports that D-glucuronic acid and glucuronic acid $\gamma$-lactone (also known as glucurono-6,3-lactone) can be applied externally to the skin, together with vitamin C and water, ethanol or aqueous ethanol as a vehicle, as a scalp care agent. In a particular experiment, Kohler reports regrowth of hair following daily application for six months of a 1% solution of D-glucuronic acid.

Kohler et al in DE OLS 26 19 100 also claims the use of glucuronic acid or glucuronic acid $\gamma$-lactone as inhibitors in agents for inhibiting the activity of $\gamma$-glucuronidase, particularly in combination with vitamin $B_{12}$. Whereas Kohler et al are concerned with $\gamma$-blucuronidase as found in unusually high concentrations in healing wounds and cancer tissues, they do state that the agents also have a beneficial effect on the loss of hair.

In experiments to be described later in this specification, we have found that both glucuronic acid and glucurono-6,3-lactone are weak inhibitors of $\gamma$-glucuronidase activity and require the presence of a second inhibitor and/or a special activity enhancer, as hereinafter defined, to provide significant hair growth or regrowth. The weak inhibition by glucuronic acid in this respect has also been confirmed by Levvy and Snaith (1972) in "Advances in Enzymology" 36 where, at page 156 they state that:

"Both β-glucuronidase and α-glucuronidase are feebly inhibited by glucuronic acid . . . "

BACKGROUND OF THE INVENTION

The above review of the most relevant references concerning the alleged promotion of hair growth following topical or systemic application of specified molecules, has prompted the study in greater detail, of the biological and biochemical mechanisms involved in the control of the hair growth cycle. The reported role of the dermal papilla which is situated at the base of the hair follicle, and the closely related cells of the connective tissue sheath which surrounds the hair follicle are alleged to be of key importance in governing the cyclic behaviour of hair follicles. This has been shown, for example, directly by Oliver R F (1970) J Embryol Exp Morphol., 23, 219-236, and the changes in the dermal papilla during the hair cycle are consistent with these observations. At the end of anagen, there is a sudden loss of fibronectin [Couchman J R and Gibson W T, (1985) Dev Biol , 108, 290-298]and metachromatic (glycosaminoglycan) staining [Montagna W et al, (1952) Q J Microsc Sci., 93, 241-245]from the connective tissue matrix of the dermal papilla which then undergoes condensation.

Conversely, expansion and elaboration of new matrix is associated with the onset of anagen. A direct role of matrix components in stimulating hair growth was suggested by the work of Meyer et al (1961), [supra].

It is accordingly apparent that glycosaminoglycan breakdown is an important early change in catagen, and since there is already evidence for a link between the presence of intact glycosaminoglycans and hair growth, we have suggested that prevention of proteoglycan and glycosaminoglycan breakdown may lead to earlier onset and/or prolongation of anagen. This would effectively retard hair loss and reverse baldness.

When considering the breakdown of glycosaminoglycans, it must be remembered that these are complex polysaccharides built up from alternating hexosamine and uronic acid units. Modification of these units by N-and/or and/or O-sulphation, and by N-acetylation provides further scope for diversity, which necessitates the concerted, sequential action of a range of enzymes for complete degradation to occur. Furthermore, glycosaminoglycans normally exist in the form of a proteoglycan, in which glycosaminoglycan chains are attached to a protein core. Degradation can therefore occur by the action of proteolytic enzymes ("proteoglycanases") on the protein core, causing release of intact glycosaminoglycan chains which are taken up by cells or removed in the circulation, or by the action of endoglycosidases, exoglycosidases and sulphatases ("glycosaminoglycanases") which cleave the glycosaminoglycan molecule at specific sites. It follows that glycosaminoglycan breakdown may be prevented in a number of ways, viz by inhibiting proteoglycanase activity, by blocking cellular uptake of intact glycosaminoglycan chains, and/or by inhibiting glycosaminoglycanase activity.

We have now identified chemical inhibitors of key enzymes and other cellular events involved respectively in the breakdown of proteoglycan or glycosaminoglycan chains, and in the blocking of cellular uptake of intact glycosaminoglycan chains.

It should be explained by "chemical inhibitor" is meant a substance that is physiologically suitable and safe for topical application to human skin, and which is capable of inhibiting proteolytic breakdown of the proteoglycans or inhibiting glycosidase or sulphatase enzymes involved in the breakdown or modification of glycosaminoglycan side chains by direct, enzyme inhibition or by protecting the substrate so that the enzyme does not recognise it, or inhibiting cellular events involved in the recognition and uptake of glycosaminoglycans.

We have accordingly found that these inhibitors will indeed stimulate hair growth as predicted on the basis of the theory outlined above.

DEFINITION OF THE INVENTION

Accordingly, the invention provides a composition suitable for topical application to mammalian skin or hair for inducing, maintaining or increasing hair growth which comprises:
(i) a first chemical inhibitor chosen from proteoglycanase inhibitors, glycosaminoglycanase inhibitors, glycosamincglycan chain cellular uptake inhibitors or mixtures thereof; and
(ii) a cosmetically acceptable vehicle for the chemical inhibitor;
provided that when the first chemical inhibitor is a weak inhibitor, such that a 1mM aqueous solution of the inhibitor reduces proteoglycanase activity, glycosaminoglycanase activity or cellular uptake of glycosaminoglycan chains, by from 5 to 50%, in accordance with at least one of the assay tests as herein described, then there is also present in the composition a second chemical inhibitor and/or an activity enhancer; provided also that when minoxidil is the sole chemical inhibitor then the activity enhancer is a penetration enhancer chosen from:
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate Benzyl benzoate
Butyl benzoate
Hexyl laurate
L- Ethyl caprate
Ethyl caprylate
Butyl stearate
Benzyl salicylate
2-hydroxypropanoic acid
2-hyroxyoctanoic acid,
esters of pyroglutamic acid having the structure:

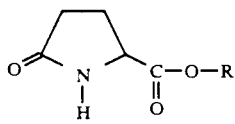  (1)

where R is $C_1$ to $C_{30}$ alkyl, or

and where R' and R" are the same or different and are each represented by H or the grouping:

$[(CH_3)_u, (CH_2OH)_v, (CH_2)_w, (CH_3CH_2)_x, (CH=CH)_z]$-  (2)

where
u is zero or 1
v is zero, or the integer 1 or 2,
w is zero, or an integer of from 1 to 21
x is zero, or an integer of from 1 to 4,
y is zero, or the integer 1 or 2,
z is zero, or an integer of from 1 to 22, and
u+v+w+x+y+z is an integer of from 1 to 22;
provided that when the subgrouping (CH=CH) is present, then the total number of carbon atoms in said grouping is from 10 to 22; and/or
a cationic polymer chosen from:
 Guar Hydroxypropyltrimonium chloride
 Quaternium-19
 Quaternium-23
 Quaternium-40
 Quaternium-57
 Poly(dipropyldiallylammonium chloride)
 Poly(methyl-β-propaniodiallylammonium chloride)
 Poly(diallylpiperidinium chloride)
 Poly(vinyl pyrinium chloride)
 Quaternised poly (vinyl alcohol) and
 Quaternised poly-(dimethylaminoethylmethacrylate);
the total amount of chemical inhibitor present in the composition being sufficient to increase hair growth in the rat, when said composition is applied topically thereto, by at least 10% more than that obtainable using a control composition from which the said inhibitors have been omitted.

DISCLOSURE OF THE INVENTION

The Chemical Inhibitor

As has already been stated, a "chemical inhibitor" is a substance which is not only physiologically suitable and safe for topical application to skin, but which is capable of inhibiting in some way proteoglycanase activity, and/or glycosaminoglycanase activity and/or cellular uptake of glycosaminoglycan chains.

It is preferred that the chemical inhibitor is one which is significantly effective in at least one of these respects, that is, it is a strong inhibitor which is normally capable at a concentration of 1mM of reducing said activity or cellular uptake by more than 50%. For less effective inhibitors, ie., weak inhibitors, which are only capable, at this concentration, of reducing said activity or cellular uptake by from 5 to 50%, then it is necessary to include in the composition according to the invention a second chemical inhibitor and/or an activity enhancer.

In view of the complexity of the proteoglycan and glycosaminoglycan chain which can be degraded in different ways with a variety of enzymes, it is necessary to screen a potential chemical inhibitor in at least one of several different assay systems. Suitable assays which can be employed for endoglycosidases, exoglycosidases, sulphatases, sulphamatases are described in "Lysosomes—A Laboratory Handbook", Second Edition (1977) edited by J. T. Dingle. Proteoglycanase inhibitors may be conveniently assayed by the method described by Nagase & Woessner (1980) in Analyst. Biochem. 107, 385. Cellular uptake inhibition may be assessed by using radioactively labelled glycosaminoglycans according to the method described by Eskild W, et al., (1986) in Int. J. Biochem. 18, 647.

Suitable assay methods for each of the relevant enzymes and their inhibition by chemical inhibitors will be described and illustrated later in this specification.

The Proteoglycanase Inhibitors

According to one embodiment of the invention, the composition comprises a direct proteoglycanase inhibitor, that is a substance which will suppress the activity of proteinase enzymes present in or in the region of the dermal papilla, and/or the connective tissue sheath of the hair follicle.

An example of a direct proteoglycanase inhibitor of this type is 1,10-phenanthroline, also identified by Galloway et al, (1983) in Biochem. J. 209, 741-742, as a bone proteoglycanas inhibitor.

Further examples of direct proteoglycanase inhibitors include various thiol, carboxyalkyl and hydroxamic peptide inhibitors, such as those described by Caputo et al., (1987) in Biochemical Pharmacology 36, 995-1002 as effective inhibitors of the action of a metalloproteinase on proteoglycan core protein. These inhibitors include:
Thiols, such as
 AcetylPhe-LeuSH
 AcetylSer-LeuSH
 AcetylTrp-LeuSH
 AcetylPhe-Phe-LeuSH
 $HSCH_2CH$(i-Butyl)$COPheNH_2$
 $HSCH_2CH$(i-Butyl)$COLeu$-$PheNH_2$
 AcetylTrp-IleSH
 AcetylPhe-IleSH
Carboxylic acids, such as
 HOOCCH(i-Butyl)Leu-Leu-LeuOCH$_3$
 HOOCCH(i-Butyl)Leu-Leu-AlaNH$_2$
 HOOCCH(i-Butyl)Leu-Leu-PheNH$_2$
 HOOCCH(i-Butyl)Leu-Leu-Leu-AlaNH$_2$
Hydroxamic acids, such as
 HONHCOCH$_2$CH(n-Pentyl)COLeu-PheNH$_2$
 HONHCOCH$_2$CH(n-Pentyl)COLeu-AlaNH
 HONHCOCH$_2$CH(i-Butyl)COLeu-PheNH$_2$
 HONHCOCH CH(n-Pentyl)COVal-AlaNH$_2$ According to a further embodiment of the invention, the composition can comprise an indirect proteoglycanase inhibitor, that is a substance which modifies the proteoglycan substrate so that the proteoglycanase does not recognise it. An example of an indirect proteoglycanase inhibitor of this type is the class of compounds defined as cationic oligomers.

According to this embodiment of the invention, there is provided a composition which comprises one or more oligomeric molecules containing one or more cationic groups which will bind to negatively charged anionic proteoglycan molecules and protect them from enzymic attack. Preferred cationic oligomers may be chosen from those which are rich in arginine and/or lysine, containing up to 20, preferably 5 to 10 amino acids in sequences similar to or the same as those found in naturally occurring basic proteins such as protamines and histones.

Specific examples of cationic oligomers are:
Arg-Arg-Arg,
Cys-Arg-Arg-Arg-Lys-Arg-Arg,
Pro-Arg-Arg-Arg-Arg, and
Arg-Pro-Val-Arg-Arg-Arg-Arg-Arg-Pro-Val.

The Glycosaminoglycanase Inhibitors

According to a further embodiment of the invention, the composition comprises a glycosaminoglycanase inhibitor chosen from endoglycosidase inhibitors, exoglycosidase inhibitors, sulphatase inhibitors, sulphamatase inhibitors and mixtures thereof.

Examples of these enzyme inhibitors, together with the relevant enzymes whose activity they inhibit, can be classified as follows:

| Chemical Class | Enzyme(s) Inhibited |
| --- | --- |
| (a) Anions (as soluble metal or ammonium salts) | |
| sulphate | idurono-sulphate sulphatase<br>sulphatases A and B;<br>heparin sulphamatase<br>N-acetylglucosamine-6-sulphate sulphatase |
| sulphite | sulphatase A;<br>heparin sulphamatase |
| pyrophosphate | sulphatase A;<br>chondroitin-6-sulphatase;<br>heparin sulphamatase |
| fluoride | sulphatase A;<br>heparin sulphamatase |
| borate | - heparin sulphamatase |
| chloride | sulphatase B;<br>chondroitin-6-sulphatase |
| gluconate | - sulphatase B |

Of the above anion inhibitors of sulphatase A or B, particularly preferred examples are sulphate and gluconate, especially in the form of magnesium sulphate and zinc gluconate respectively.

(b) Aldonolactones and esterified aldonolactones having the structure:

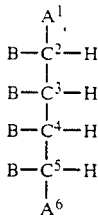

where
$A^1$ and $A^6$ are —H, $$-CH_3, \quad -\overset{OR'}{\underset{|}{C}}=O \text{ or } -\overset{OR}{\underset{|}{C}}=O$$

B is OR" or a lactone linkage to position 1 or 6, or —NHCOCH$_3$
and where R is -H or C$_2$ to C$_8$ alkyl,
R' is the remainder of the molecule joined through another C atom at positions 2 to 5 to form a lactone,
R" is —H or C$_2$ (ie acetyl) to C$_4$ acyl of either configuration with respect to the backbone of this molecule.

Preferred examples of aldonolactones which inhibit the exoglycosidases, as specified, are as follows:

| | Enzyme(s) inhibited |
| --- | --- |
| L-Galactono-1,4-lactone | β-galactosidase<br>β-N-acetylhexosaminidase |
| L-Arabino-1,5-lactone | β-galactosidase |
| D-Fucono-1,5-lactone | β-galactosidase |
| D-Glucaro-1,4-lactone | β-glucuronidase<br>α-L-iduronidase |
| D-Glucurono-6,3-lactone | β-glucuronidase |
| Galactaric acid lactone | β-glucuronidase<br>α-L-iduronidase |
| 2-Acetamido-2-deoxygluconolactone | β-N-acetylhexosaminidase |
| 2-Acetamido-2-deoxygalactonolactone | β-N-acetylhexosaminidase |
| D-Glucaro-1,4:6,3-dilactone | β-glucuronidase<br>α-L-iduronidase |
| L-Idaro-1,4-lactone | α-L-iduronidase |

Preferred examples of esterified forms of aldonolactones which give a more sustained inhibitory effect are:

| | |
| --- | --- |
| 2,3,5-Tri-O-acetyl-D-glucaro-1,4-lactone | β-glucuronidase<br>α-L-iduronidase |
| 2,5-Di-O-acetyl-D-glucaro-1,4:6,3-dilactone | β-glucuronidase<br>α-L-iduronidase |

(c) Monosaccharides and esterified monosaccharides having the structure:

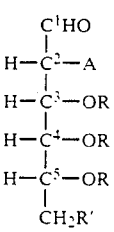

where

A is —OR or —NHCOCH₃
R is —H, —SO₃M, C₂ (ie acetyl) to C₄ acyl
R' is —H or —OR
M is —H or a metal cation.

Functional groups can be in either configuration with respect to the backbone of the above molecule.

Preferred examples of monosaccharides and esters thereof which inhibit exoglycosidases or a sulphatase, as specified, are as follows:

| Monosaccharide/esters | Enzymes(s) inhibited |
| --- | --- |
| N-Acetylglucosamine | α-N-acetylglucosaminidase<br>β-galactosidase<br>β-N-acetylhexosaminidase |
| N-Acetylgalactosamine | β-galactosidase<br>β-N-acetylhexosaminidase |
| D-Galactosamine | β-N-acetylhexosaminidase |
| D-Glucosamine-3-sulphate | Sulphatase 'B' |
| N-Acetylmannosamine | α-N-acetylglucosaminidase |

(d) Piperidines having the structure:

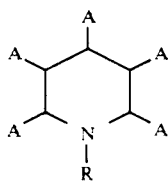

where
A is —H, —OR' or

R is —H, C₂ to C₈ alkyl or diamino-pyrimidine N-oxide
R' is —H or C₂ (ie acetyl) to C₄ acyl;
substituent groups A can be identical or can be represented by 2 or 3 of the groups defined above on the same ring structures. They can also be in either configuration with respect to the plane of the ring.

Preferred examples of piperidines which inhibit exoglycosidases, as specified, are as follows:
Minoxidil which inhibits the enzyme β-glucuronidase and
2(S)-Carboxy-3(R),4(R),5(S)-trihydroxypiperidine which inhibit the enzymes β-glucuronidase and α-L-iduronidase.

(e) examples of substances which inhibit the activity of the endoglycosidase hyaluronate endoglycosidaminidase are:
Phosphorylated hesperidin
sodium aurothiomalate
substituted thiosemicarbazone indoles, and
mixtures thereof.

The glycosaminoglycan chain cellular uptake inhibitors

According to a further embodiment of the invention, the composition comprises an inhibitor of cellular uptake of glycosaminoglycan chains which prevents recognition and binding events at the cell surface by competing with glycosaminoglycan chains, or by modification of the chains so that they are no longer recognised by the cell.

An example of this class of inhibitors is given by hexuronic acid and esters thereof which may be represented by the generic structure:

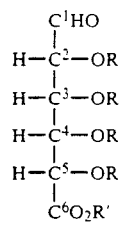

where R is —H, —SO₃M, C₂ (ie acetyl) to C₄ acyl; R' is —H or C₂ to C₈ alkyl.

Functional groups can be in either configuration with respect to the backbone of the above molecule.

Preferred inhibitors belonging to this class are glucuronic acid, iduronic acid and esters thereof.

The total amount of chemical inhibitor present in the composition according to the invention is sufficient to increase hair growth in the rat, the model selected for this test, when said composition is applied topically thereto, by at least 10% more than that obtainable using a control composition from which the said inhibitors have been omitted.

Preferably, the amount of chemical inhibitor should be sufficient to increase hair growth in the rat by at least 20%, more preferably by at least 30%, most preferably by at least 40% and ideally by at least 50%.

The sufficient amount will depend on the effectiveness of a chemical inhibitor, some being more effective than others, but in general, an amount of from 0.0001 to 99%, preferably from 0.1 to 20% by weight of the composition will provide an adequate dose to the skin after topical application.

Compositions containing minoxidil

Minoxidil is a weak inhibitor of β-glucuronidase activity and accordingly, when minoxidil is present in the composition, then there is also present a second chemical inhibitor and/or an activity enhancer.

Particularly preferred mixtures of minoxidil and a second chemical inhibitor include the following:
Minoxidil and Zinc gluconate
Minoxidil and Magnesium sulphate
Minoxidil and D-glucaro-1,4-lactone
Minoxidil and 1,10-phenanthroline
Minoxidil and D-glucosamine-3-sulphate
Minoxidil and L-idaro-1,4-lactone
Minoxidil and L-galactono-1,4-lactone
Minoxidil and 2-acetamido-2-deoxygluconolactone
Minoxidil and D-glucaro-1,4:6,3-dilactone
Minoxidil and 2,3,5-tri-O-acetyl-D-glucaro-1,4-lactone
Minoxidil and N-acetylglucosamine
Minoxidil and N-acetylmannosamine
Minoxidil and phosphorylated hesperidin
Minoxidil and glucuronic acid When minoxidil is the sole chemical inhibitor present in the composition according to the invention, then a special condition on its use in accordance with the invention prevails in that the activity enhancer which must accompany minoxidil, preferably in an amount sufficient to enhance significantly the hair growth activity of minoxidil, in the composition, is chosen from a limited selection of materials, referred to in detail later in this specification, namely certain penetration enhancers and certain cationic polymers.

The Vehicle

The composition according to the invention also comprises a solid, semi-solid or liquid cosmetically and/or physiologically acceptable vehicle, to enable the inhibitor to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the chemical inhibitors which therefore ensure that they can be applied to and distributed evenly over the hair and/or scalp at an appropriate concentration. The vehicle is preferably one which can aid penetration of the inhibitors into the skin to reach the immediate environment of the hair follicle. Compositions according to this invention can include water as a vehicle, and/or at least one cosmetically acceptable vehicle other than water.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The amount of vehicle in the composition, including water if present, should preferably be sufficient to carry at least a portion of a selected chemical inhibitor to the skin in an amount which is sufficient effectively to enhance hair growth. The amount of the vehicle can comprise the balance of the composition, particularly where little or no other ingredients are present in the composition. Accordingly, the vehicle or vehicles can comprise from 1 to 99.99%, preferably from 50 to 99.5% and ideally from 90 to 99% by weight of the composition.

Perfume

The composition according to the invention can also optionally comprise a perfume in an amount sufficient to make the composition acceptable to the consumer and pleasant to use. Usually, the perfume will form from 0.01 to 10% by weight of the composition.

Activity Enhancer

The composition according to the invention can also optionally comprise an activity enhancer, especially when the chemical inhibitor is a weak inhibitor.

The activity enhancer can be chosen from a wide variety of molecules which can function in different ways to enhance the hair growth effects of the chemical inhibitor. Particular classes of activity enhancers include other hair growth stimulants, penetration enhancers and cationic polymers, whose presence can further improve the delivery of the chemical inhibitor through the stratum corneum to its site of action in the immediate environment of the hair follicle.

Some activity enhancers can also function as vehicles for the chemical inhibitor.

(a) Other Hair Growth Stimulants

Examples of other substances which themselves possess the ability to stimulate or increase hair growth include, for example;
Benzalkonium chloride
Benzethonium chloride
Phenol
Estradiol
Diphenhydramine hydrochloride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Panthenol
Castor oil
Hinokitiol
Prednisolone
Resorcinol Further substances which themselves possess the ability to increase the rate of terminal hair growth include: α-1,4esterified disaccharides described by Choay S.A. in EP-A-O 064 012, having the structure:

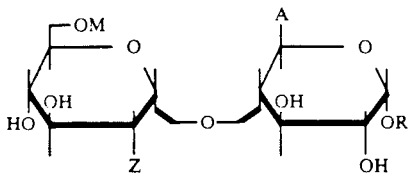

where
Z represents a functional nitrogen group, such as an azide or a group having the structure —NHB, in which B represents —H or a functional group such as acetyl or sulphate as a salt with an organic or mineral cation;
M represents —H or $SO_3M_1$, where $M_1$ is an organic or metallic cation, particularly an alkali metal; or an acetyl group;
R represents a $C_1$ to $C_4$ alkyl radical, especially methyl; or an aryl radical;
A represents a functional group such as an acid or —$COOR_1$, where $R_1$ represents —H or a $C_1$ to $C_4$ alkyl radical, especially methyl; or a metal, especially an alkali metal;
esterified oligosaccharides as described by Unilever in EP-A-0 211 610, including at least one esterified disaccharide unit consisting of a uronic acid residue having the structure:

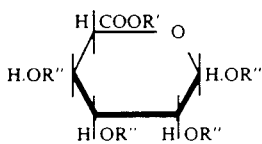

and a hexosamine residue having the structure:

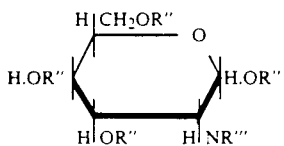

where
R' is —H, $C_3$ to $C_{10}$ alkyl or

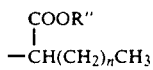

R" is —H, $C_1$ to $C_4$ alkyl, —$CO(CH_2)_mCH_3$, —$SO_3M$,
R'" is —H, —$CO(CH_2)_mCH_3$, or —$SO_3M$,
M is —H, or a metallic or organic cation
n is 0 or an integer of from 1 to 7, and
m is 0 or the integer 1 or 2;
the groups designated R" being the same or different, one R" group from each pyranose ring structure being linked by a glycosidic linkage having the configuration α-1,3, α1,4, β-1,3 or β-1,4; and the —COOR', —CH$_2$OR" and —OR" groups being of either configuration with respect to the pyranose rings;

Minoxidil glucuronides, as described by Unilever in EP-O 242 967,

Minoxidil sulphates, as described by The Upjohn Co. in WO 86/04231.

(b) Penetration Enhancers

As has been stated earlier, the presence of a penetration enhancer can potentiate the benefit of the chemical inhibitor, by improving its delivery through the stratum corneum to its site of action in the immediate environment of the hair follicle close to the dermal papilla.

The penetration enhancer can accordingly function in a variety of ways. It can for example, improve the distribution of the hair growth promoter on the skin surface or, it can increase its partition into the skin from the composition when applied topically, so aiding its passage to its site of action. Other mechanisms enhancing the benefit of the chemical inhibitor may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate Butyl stearate
Benzyl salicylate
2-hydroxypropanoic acid
2-hyroxyoctanoic acid, Yet further penetration enhancers include esters of pyroglutamic acid having the structure:

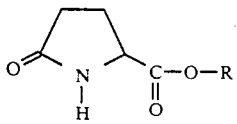

(1)

where R is $C_1$ to $C_{30}$ alkyl, or

and where R' and R" are the same or different and are each represented by H or the grouping.

$$[(CH_3)_u, (CH_2OH)_v, (CH_2)_w, (CH_3CH_2)_x, (CH\equiv CH)_z]-$$ (2)

where
u is zero or 1
v is zero, or the integer 1 or 2,
w is zero, or an integer of from 1 to 21
x is zero, or an integer of from 1 to 4,
y is zero, or the integer 1 or 2,
z is zero, or an integer of from 1 to 22, and
$u+v+w+x+y+z$ is an integer of from 1 to 22;
provided that when the subgrouping (CH=CH) is present, then the total number of carbon atoms in said grouping is from 10 to 22.

Examples of suitable esters of pyroglutamic acid where R in structure (1) is $C_1$ to $C_{30}$ alkyl are:
pyroglutamic acid methyl ester
pyroglutamic acid ethyl ester
pyroglutamic acid n-propyl ester
pyroglutamic acid n-butyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradcyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester Particularly preferred esters of this group are those where R in structure (1) is $C_1$ to $C_{14}$ alkyl, (linear or branched), especially $C_1$ to $C_6$ (linear or branched).

Further examples of preferred esters of pyroglutamic acid, where R in structure (1) is

are those where R' and/or R" having the structure shown for grouping (2), include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl, and
arachidyl.
and the $C_{10-22}$ alkenyl groups:
linoleyl
linolenyl
γ-linolenyl
arachidonyl, and
Columvinyl.

Further examples of the grouping (2) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

It is to be understood that the above list is not exhaustive, there being many other examples of alkyl or substituted alkyl groups expressed by the above generic grouping (2).

Further specific examples of esters of pyroglutamic acid which are particularly suited to use as penetration enhancers are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above lists of specific examples of esters of pyroglutamic acid are not exhaustive, there being many other examples expressed by the generic structure of these esters.

Further examples of penetration enhancers include:
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one
Further examples of penetration enhancers include surface active agents, preferred examples of which include:

(i)

Anionic surface active agents, such as metallic or alkanolamine salts of fatty acids for example sodium laurate and triethanolamine oleate;

alkyl benzene sulphonates, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinates, for example sodium dioctyl sulphonsuccinate;
monoglyceride sulphates, for example sodium glyceryl monostearate monosulphate;
isethionates, for example sodium isethionate;
methyl taurides, for example Igepon T;
acylsarcosinates, for example sodium myristyl sarcosinate;
acyl peptides, for example Maypons and Lamepons;
acyl lactylates,
polyalkoxylated ether glycollates, for example trideceth-7 carboxylic acid;
phosphates, for example sodium dilauryl phosphate.

(ii)

Cationic surface active agents, such as amine salts, for example sapamin hydrochloride;
quartenary ammonium salts, for example Quaternium 5, Quaternium 31 and Quaternium 18;

(iii)

Amphoteric surface active agents, such as imidazol compounds, for example Miranol;
N-alkyl amino acids, such as sodium cocaminopropionate and asparagine derivatives;
betaines, for example cocoamidopropylbetaine (iv)

Nonionic surface active agents, such as fatty acid alkanolamides, for example oleic ethanolamide;
esters of polyalcohols, for example Span;
polyglycerol esters, for example that esterified with $C_{12-18}$ fatty acids and one or several OH groups;
polyalkoxylated derivatives, for example polyoxypolyoxyethylene stearate, and octylphenoxy polyethoxyethanol (TRITON X-100);
ethers, for example polyoxyethylene lauryl ether;
ester ethers, for example Tween;
amine oxides, for example coconut and dodecyl dimethyl amine oxides.

Mixtures of two or more of the above surface active agents can be employed in the composition according to the invention.

(c) cationic polymers chosen from:
Guar Hydroxypropyltrimonium chloride
Quaternium-19
Quaternium-23
Quaternium-40
Quaternium-57
Poly(dipropyldiallylammonium chloride)
Poly(methyl-$\beta$-propaniodiallylammonium chloride)
Poly(diallylpiperidinium chloride)
Poly(vinyl pyridinium chloride)
Quaternised poly (vinyl alcohol)
Quaternised poly (dimethylaminoethylmethacrylate); and
mixtures thereof It is to be understood that even when a strong chemical inhibitor is employed, then it is also desirable, though not essential, to incorporate an activity enhancer in the composition according to the invention, in order further to enhance its benefit in increasing the hair growth.

The amount of activity enhancer, when employed in accordance with the invention, will normally be from 0.1 to 50%, preferably from 0.5 to 25% and most preferably from 0.5 to 10% by weight of the composition.

Further preferred embodiments of the invention

Further preferred embodiments of the invention are those where the composition according to the invention comprises an activity enhancer in addition to at least one chemical inhibitor.

Particularly preferred mixtures of chemical inhibitors and activity enhancers include the following, where minoxidil as a less effective chemical inhibitor, as herein defined, should be employed in compositions according to the invention with an activity enhancer.

Accordingly, preferred mixtures are:
Minoxidil and diisopropyl sebacate
Minoxidil and pyroglutamic acid methyl ester
Minoxidil and pyroglutamic acid n-propyl ether
Minoxidil and 2[pyroglutamoyloxy]-propionic acid
Minoxidil and ethyl-2-[pyroglutamoyloxy]-n-propionate
Minoxidil and 2-hydroxy octanoic acid Other hair growth promoter adjuncts The composition according to the invention can also contain adjuncts other than those already mentioned, depending on the form of the intended product. It is, for example, possible to include antiseptics, preservatives, antioxidants, emulsifiers and colouring agents, which can improve the stability and consumer appeal of the composition.

The composition according to the invention can also be employed as a vehicle for a wide variety of cosmetically or pharmaceutically active ingredients, particularly ingredients which have some beneficial effect other than the promotion of hair growth when applied to the skin.

Process

The invention also provides a process for the preparation of a composition suitable for topical application to mammalian skin or hair which comprises mixing a chemical inhibitor as herein defined, with a suitable vehicle to provide a composition according to the invention, in which the inhibitor forms from 0.0001 to 99% by weight of the composition.

Product Form and Container

The compositions of the invention can be formulated as liquids, for example as a lotion, shampoo, milk or cream for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example sticks, creams or gels, for use in conjunction with a suitable applicator or simply a tube, bottle or lidded jar, or as a liquid-impregnated fabric, such as a tissue wipe.

The invention accordingly also provides a closed container containing a composition as herein defined.

Use of the Chemical Inhibitor for Inducing, Maintaining or Increasing Hair Growth The invention also provides for the use of a chemical inhibitor, as herein defined, for topical application to mammalian skin or hair for inducing, maintaining or increasing hair growth.

The compositions according to the invention are primarily intended for topical application to the scalp of the human subject, particularly where the head is already bald or balding, in order to promote the regrowth of terminal hair. The compositions can also be applied profilactically to the hair and hence the scalp to reduce or prevent the onset of baldness.

The amount of the composition and the frequency of application to the hair and/or scalp can vary widely, depending on personal needs, but it is suggested as an example that topical application of from 0.1 to 5g daily containing from 0.00001 to 1 g of a selected chemical inhibitor over the period of at least six months will in most cases result in an improvement in hair growth.

EVALUATION OF EFFICACY OF CHEMICAL INHIBITORS USING THE RAT MODEL (i) Measurement of hair growth using the rat model The effect of compounds on hair growth was assessed using male rats as an animal model as follows. In each of the comparisons reported below, 10 rats were used.

A small patch of normal skin (4cm ×4cm) on the upper back of each rat was clipped at the start of the experiment and a hair growth stimulant composition (or a control) applied twice daily topically to the clipped area. Hair was clipped from the area of the patch twice weekly, collected and weighed at each time point, and cumulative hair weight calculated. From these data, it was possible to estimate the effect of a chemical inhibitor as a test compound on the amount and duration of hair growth during the experiment. A positive response, ie. an increase of at least 10% by weight of hair, compared with a control, indicates the potential of the test substance to prevent hair loss and/or reverse baldness in human subjects.

(ii) Validation of rat model for hair growth using Minoxidil

The rat model was validated by showing that topical application of a known promoter of human hair regrowth, namely 2% (w/v) minoxidil in a vehicle of 70% ethanol, 20% water and 10% propylene glycol, caused a significant increase of 55% in hair growth as shown below:

TABLE 1

| Treatment | Mean Cumulative Hair weight (mg) ± sd. after 45 days | Significance Level (vs vehicle) |
| --- | --- | --- |
| 2% minoxidil | 599.2 ± 85.1 | p = 0.001* |
| Vehicle (control) | 387.3 ± 75.9 | |

*statistically significant (iii) Measurement of hair growth following topical application of D-glucaro-1,4-lactone as enzyme inhibitor Topical treatment with a composition according to the invention was found to stimulate hair growth. In this example, the effect of topical application of D-glucaro-1,4-lactone, an inhibitor of $\beta$-glucuronidase is shown. The test solution in this experiment contained approximately 7% (w/v) of the glucarolactone in the form of an equilibrium mixture prepared from boiled calcium glucarate. The vehicle was 33% (v/v) ethanol containing 50mM Na citrate at pH 4.2. Test or control solutions (0.3ml) were applied twice-daily to the clipped site; the hair growth results are shown below in Table 2.

TABLE 2

| Treatment | Mean Cumulative Hair weight (mg) ± sd. after 45 days | Significance Level (vs vehicle) |
| --- | --- | --- |
| 7% Glucarolactone | 482.7 ± 58.4 | p < 0.05* |
| Vehicle (control) | 427.2 ± 58.7 | |

*statistically significant

In addition to demonstrating a statistically significant stimulation of hair growth (a 13% increase) as shown in Table 2, glucarolactone has been consistently found to advance the onset of anagen, thus reducing the amount of time spent in the resting stage of hair cycle.

(iv) Synergistic interaction of D-glucaro-1,4-lactone and minoxidil in hair growth In other experiments, glucarolactone has been found to display a synergistic effect on hair growth in combination with a low concentration of minoxidil. Both glucarolactone and minoxidil are $\beta$-glucuronidase inhibitors. This effect is illustrated in Table 3 below, in which the vehicle was 33% v/v ethanol in 50mM sodium citrate, pH4.2:

TABLE 3

| Treatment | Mean Cumulative hair weight (mg) ± sd. after 45 days | Signif- icance level (vs vehicle) | Increase in hair growth (%) (Test vs control) |
|---|---|---|---|
| 7% glucarolactone (GL) | 482.7 ± 58.4 | p < 0.05* | 13 |
| 0.2% minoxidil (M) | 465.8 ± 48.8 | p > 0.1 | 9 |
| 7% GL + 0.2% M | 561.1 ± 57.7 | p = 0.001* | 31 |
| Vehicle (control) | 427.2 ± 58.7 | | |

*statistically significant

From these results, it can be seen that the hair growth properties of minoxidil alone (9% increase in hair growth), can be greatly enhanced when the glucarolactone is present (31% increase in hair growth), thus making possible the use of a lower than usual concentration of minoxidil (for example, 0.2% by weight which is water soluble, instead of 2% by weight which is not) without diminishing its ability to stimulate hair growth. The statistical significance of this synergistic effect can be deduced from the results shown in Table 3 above, when it is realised that the mean of GL+M was compared with either GL (p < 0.01) or M (p=0.001) alone.

A further advantage of using a composition containing a lower than usual concentration of minoxidil is the enhanced in-use safety margin, bearing in mind possible contra-indications which alledgedly follow topical application of higher concentrations of minoxidil.

(v) Influence of 1-methylpyrrolidone as activity enhancer in the stimulation of hair growth with glucarolactone In a further experiment, glucarolactone was tested in the presence of an activity enhancer, 1-methylpyrrolidone. Again, a significant increase in hair weight was obtained, as shown below in Table 4, in which the vehicle was 33% v/v aqueous ethanol containing 50mM Na citrate buffer pH4.2 and 10% w/v 1-methylpyrrolidone.

TABLE 4

| Treatment | Mean Cumulative Hair Weight (mg) ± sd, after 46 days | Significance Level (vs vehicle) |
|---|---|---|
| 7% glucarolactone | 706.2 ± 86.6 | p < 0.01* |
| vehicle (control) | 611.1 ± 48.1 | |

*statistically significant

This represents a 15% increase in hair growth.

(vi) Influence of the wetting agent Triton X-100 as an activity enhancer in the stimulation of hair growth with glucarolactone In a further experiment, the inclusion of a surface active agent, Triton X-100 was found to provide a particularly advantageous activity enhancer for glucarolactone, as shown below in Table 5, in which the vehicle was 20% v/v ethanol containing 50mM sodium citrate, pH4.2 and 0.1% w/v Trion X-100.

| Treatment | Mean Cumulative Hair Weight (mg) ± sd. after 43 days | Significance Level (vs vehicle) |
|---|---|---|
| 7% glucarolactone | 573.3 ± 82.5 | p = 0.001* |

-continued

| Treatment | Mean Cumulative Hair Weight (mg) ± sd. after 43 days | Significance Level (vs vehicle) |
|---|---|---|
| vehicle (control) | 412.3 ± 57.5 | |

*statistically significant

This represents a 39% increase in hair growth.

(vii) Influence of Zinc gluconate as an inhibitor of Sulphatase B in the stimulation of hair growth In another experiment, the effect of sulphatase B inhibitor, zinc gluconate was examined and found to produce a significant increase in hair weight as shown below in Table 6, in which the vehicle was 20% aqueous ethanol.

TABLE 6

| Treatment | Mean Cumulative Hair Weight (mg) ± sd. after 45 days | Significance Level (vs vehicle) |
|---|---|---|
| 2% (w/v) zinc gluconate | 460.9 ± 45.7 | p < 0.05* |
| vehicle (control) | 397.8 ± 56.3 | |

*statistically significant

This represents a 16% increase in hair growth.

Assay of enzyme activity and cellular uptake, and inhibition thereof with the chemical inhibitor It is a feature of the invention that the chemical inhibitor is one whose inhibition of proteoglycanase activity, glycosaminoglycanase activity or cellular uptake of glycosaminoglycans chains is such that a 1 mM aqueous solution of the inhibitor reduces said activity or said cellular uptake by more that 50% as measured by an appropriate assay.

For chemical inhibitors which are less effective in that at the same concentration, they reduce said activity or said cellular uptake by from 5 to 50%, it is then necessary to include also a second chemical inhibitor and/or an activity enhancer as herein defined, which will not necessarily increase said activity or said cellular uptake, as measured in vitro, but which will nevertheless further enhance hair growth, often synergistically.

In each of the assays referred to herein, the chemical inhibitor was tested at a pH close to the optimum pH value of the relevant enzyme, and under conditions of saturating substrate concentration, to ensure that $V_{max}$ was obtained in the controls.

The relevant assays employed to assess the ability of chemical inhibitors to inhibit enzyme activity or cellular uptake are as follows:

1. Proteoglycanase assay

The degradation of proteoglycan by proteoglycanase and its inhibition was determined using the method described by Nagase & Woessner in Analyt. Biochem., 107, 385 (1980).

2. Glycosaminoglycanase assay

In view of the complexity of the glycosaminoglycan chain, several different enzymes are known to cleave this chain at different points. Glycosaminoglycanases, can accordingly be classified into exoglycosidases, endoglycosidases, sulphatases and sulphamatases. Different assay methods were used for each of these classes. These methods are outlined below.

2.1 Exoglycosidases
2.1.1 β, N-acetylhexosaminidase
2.1.2 β-glucuronidase
2.1.3 β-galactosidase
2.1.4 α-N-acetylglucosaminidase The activity of each of these four exoglycosidases was measured using a method described in "Lysosomes, A Laboratory Handbook", edited by Dingle J.T., Second Edition, (1977) at page 118.

2.1.5 α-L-iduronidase

The activity of α-L-iduronidase was measured using Method II described by Dingle J.T. [Ibid., at page 119].

2.2 Endoglycosidase 2.2.1 Hyaluronate endoglycosidaminidase

The activity of hyaluronate endoglycosaminidase, also known as hyaluronidase was assayed by the method described by Dingle J.T [Ibid., at page 116].

2.2.2 Heparan sulphate endoglycosidase

The activity of heparan sulphate endoglycosidase was assayed by the method described by Hook et al., (1975) in Biochem. Biophys. Res. Commun. 67, 1422–1428.

3. Sulphatases and Sulphamatases 3.1 Sulphatase A and Sulphatase B

The activity of sulphatase A and B was measured using the method described by Dingle J.T. [Ibid., at page 115].

3.2 Chondroitin-6-Sulphatase

The activity of chondroitin-6-sulphatase was measured using the method reported by Singh et al (1976) in J. Clin. Invest. 57, 1036–1040.

3.3 Idurono-sulphate sulphatase

The activity of idurono-sulphate sulphatase was measured using the method reported by Lim et al (1974) in Carbohyd. Res. 37, 103–109.

3.4 Heparin Sulphamatase

The activity of heparin sulphamatase was measured using the method reported by Friedman and Arsenis (1972) in Biochem. Biophys. Res. Commun. 48, 1133–1139.

3.5 N-Acetylglucosamine-sulphate sulphatase

The activity of N-acetylglucosamine sulphate sulphatase was measured using the method reported by Habuchi et al (1979) in J.Biol. Chem., 254 7570–7578.

4. Inhibition of cellular uptake of glycosaminoglycan chains

The inhibition of cellular uptake of glycosaminoglycan chains was measured using the method reported by Eskild et al., (1986) in Int. J. Biochem. 18, 647–651.

The inhibitory effect of minoxidil on β-glucuronidase activity

The ability of minoxidil to inhibit the activity of β-glucuronidase was evaluated by the method reported by Dingle J.T. [Ibid., page 118] as described herein.

The results using different concentrations of minoxidil when incubated with a mixture of this enzyme and the nitrophenyl glucuronide substrate were as follows:

| Minoxidil concentration | | % inhibition of |
|---|---|---|
| mg/ml | mM | β-glucuronidase |
| 0.05 | 0.24 | 2 |
| 0.4 | 1.9 | 12 |
| 0.8 | 3.8 | 23 |

The percent inhibition of a 1mM concentration of minoxidil is accordingly 6%. This confirms that minoxidil is a weak enzyme inhibitor and, in accordance with the composition of the invention, when the inhibitory effect of an inhibitor is between 5 and 50%, as herein defined, then it is necessary to include in a composition containing minoxidil, a second chemical inhibitor and/or an activity enhancer.

The inhibitory effect of glucuronic acid and glucurono-6,3-lactone on β-glucuronidase activity The ability of glucuronic acid and glucurono-6,3-lactone to inhibit the activity of β-glucuronidase was also evaluated by the method reported by Dingle J.T. [Ibid., page 118].

The results when the acid or the lactone were incubated with a mixture of this enzyme and the nitrophenyl glucuronide substrate were as follow:

| Inhibitor | Inhibitor concentration | | % inhibition of |
|---|---|---|---|
| | mg/ml | mM | β-glucuronidase |
| Glucuronic acid | 0.2 | 1.03 | 20 |
| Glucurono-6,3-lactone | 0.2 | 1.14 | 51 |

The percentage inhibition of a 1mM concentration of glucuronic acid is accordingly 19.4 and that of glucurono-6,3-lactone is 44.7. This confirms that both glucuronic acid and glucurono-6,3-lactone are weak enzyme inhibitors and, in accordance with the composition of the invention, when the inhibitory effect of an inhibitor is between 5 and 50%, as herein defined, then it is necessary to include in such a composition a second chemical inhibitor and/or an activity enhancer.

EXAMPLES

The invention is illustrated by the following examples:

EXAMPLE 1

This Example illustrates a lotion according to the invention which is suitable for topical application to the scalp in order to promote hair growth.

The lotion has the following formulation:

| | % w/w |
|---|---|
| L-Galactono-1,4-lactone | 0.1 |
| ethanol | 99.995 |
| perfume | q.s. |

EXAMPLE 2

This Example illustrates a hair tonic which is suitable for application to hair or scalp.

The hair tonic has the following formulation:

| | % w/w |
|---|---|
| L-Arabino-1,5-lactone | 0.8 |

| | % w/w |
|---|---|
| ethanol | 50 |
| water | 49 |
| perfume | q.s. |

EXAMPLE 3

This Example also illustrates a lotion which is suitable for topical application to the scalp.

The lotion has the following formulation:

| | % w/w |
|---|---|
| D-Fucono-1,5-lactone | 1.5 |
| propan-2-ol | 10 |
| ethanol | 88.5 |
| perfume | q.s. |

EXAMPLE 4

This Example also illustrates a hair tonic which is suitable for application to hair or scalp.

The hair tonic has the following formulation:

| | % w/w |
|---|---|
| D-Glucaro-1,4-lactone | 0.2 |
| ethanol | 40 |
| water | 59.80 |
| perfume | q.s. |

EXAMPLES 5 to 8

The following formulations represent lotions which can be used topically in the treatment of bald or balding male or female heads.

| | % w/w | | | |
|---|---|---|---|---|
| | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| D-Glucaro-1,4:6,3-dilactone | 5 | — | — | — |
| L-Idaro-1,4-lactone | — | 1 | — | — |
| D-Glucurono-6,3-lactone | — | — | 0.8 | — |
| Galactaric acid lactone* | — | — | — | 0.6 |
| Perfume | 1 | 1 | 1 | 1 |
| Water to | 100 | 100 | 100 | 100 |

*1,2,5-tri-O-acetyl-D-glucurono-6,3-lactone

EXAMPLES 9 to 12

The following formulations represent creams which can be used in the treatment of baldness.

| | % w/w | | | |
|---|---|---|---|---|
| | 9 | 10 | 11 | 12 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and | — | — | — | 4 |

| | % w/w | | | |
|---|---|---|---|---|
| | 9 | 10 | 11 | 12 |
| stearic acids | | | | |
| N-Acetylglucosamine-lactone* | 2 | — | — | — |
| N-Acetylgalactosamino-lactone⁺ | — | — | — | 1 |
| N-Acetylglucosamine | — | 1.5 | — | — |
| A-Acetylgalactosamine | — | — | 2 | — |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| Perfume | q.s. | q.s. | q.s. | q.s. |
| Water to | 100 | 100 | 100 | 100 |

*2-Acetamido-2-deoxygluconolactone
⁺2-Acetamido-2-deoxygalactonolactone

EXAMPLE 13

This Example illustrates a water-in-oil high internal phase emulsion containing a glycosaminoglycanase inhibitor according to the invention.

The emulsion consisted of 10% by volume oily phase and 90% by weight aqueous phase.

The oily phase and the aqueous phase had the following constitution:

| | % w/w |
|---|---|
| Oily phase | |
| Sorbitan monooleate | 20 |
| Quartenium-18 hectorite | 5 |
| Liquid paraffin | 75 |
| Aqueous phase | |
| D-Glucosamine-3-sulphate | 0.5 |
| Xanthan gum | 1 |
| Preservative | 0.3 |
| Perfume | q.s. |
| Sodium chloride (1% w/w solution) to | 100 |

The emulsion was prepared by taking 10 parts by volume of the oily phase and to it adding slowly with stirring 90 parts by volume of the aqueous phase.

The high internal phase water-in-oil emulsion so formed can be applied topically to the scalp, to improve hair growth and regrowth.

The following examples 14 to 18 illustrate shampoos for use in washing the hair and scalp, and for promoting hair growth on the scalp.

EXAMPLE 14

| | % w/w |
|---|---|
| Sodium lauryl ether sulphate (2 EO) [21% AD] | 41.4 |
| Lauryl dimethylamino acetic acid betaine: [30% AD] | 4 |
| Coconut fatty acid diethanolamine | 1.5 |
| Oleyl triethoxy phosphate (BRIPHOS 03D) | 1 |
| Polyglycol-polyamine condensation resin (POLYQUART H) [50% active] | 1.5 |
| Preservative, colouring matter, salt | 0.58 |
| 2(S)-Carboxy-3(R),4(R),5(R)-trihydroxy piperidine | 5 |
| Perfume | q.s. |
| Water to | 100 |

EXAMPLE 15

|  | % w/w |
|---|---|
| Sodium lauryl ether sulphate (2 EO) [100% AD] | 12 |
| POLYMER JR400 | 2.5 |
| BRIPHOS O3D | 2.5 |
| D-Glucaro-1,4:6,3-dilactone | 4 |
| Magnesium Sulphate | 5 |
| Perfume | q.s. |
| Water to | 100 |

EXAMPLE 16

|  | % w/w |
|---|---|
| Monoethanolamine lauryl sulphate: [100% AD] | 20 |
| JAGUAR C13S | 3 |
| BRIPHOS O3D | 1.7 |
| Coconut diethanolamide | 5 |
| D-Glucaro-1,4-lactone | 1 |
| Zinc gluconate | 3 |
| Perfume | q.s |
| Water to | 100 |
| pH adjusted to 6.5 | |

EXAMPLE 17

|  | % w/w |
|---|---|
| Sodium lauryl ether sulphate (3 EO): [100% AD] | 12 |
| JAGUAR C13S | 0.3 |
| BRIPHOS O3D | 1 |
| N-Acetylglucosamine | 2 |
| Sodium chloride | 4 |
| Perfume | q.s. |
| Water to | 100 |
| pH adjusted to 6.5 | |

EXAMPLE 18

|  | % w/w |
|---|---|
| Sodium lauryl ether sulphate (2 EO) [100% AD] | 12 |
| POLYMER JR400 | 3 |
| BRIPHOS O3D | 1 |
| Opacifier | 9 |
| Magnesium sulphate | 5 |
| Perfume | q.s. |
| Water to | 100 |
| pH adjusted to 6.5 | |

EXAMPLES 19 to 24

The following Examples 19 to 24 illustrate powder compositions according to the invention which can be applied topically to the scalp.

|  | % w/w | | | | | |
|---|---|---|---|---|---|---|
|  | 19 | 20 | 21 | 22 | 23 | 24 |
| Chemically modified starch | 5 | — | 5 | — | 5 | — |
| Chemically modified cellulose | — | 5 | — | 5 | — | 5 |
| Boric acid | 10 | 10 | 10 | 10 | 10 | 10 |
| Zinc oxide | 5 | 5 | 5 | 5 | 5 | 5 |
| D-Glucaro-1,4-lactone | 3 | 2 | 5 | 1 | — | — |
| Minoxidil glucuronide | 5 | 10 | 2 | 4 | 3 | 5 |
| D-Glucaro-1,4:6,3-dilactone | — | — | — | 2 | 5 | 3 |
| Perfume | q.s. | q.s. | q.s. | q.s. | q.s. | q.s. |
| Chalk | 10 | 10 | 10 | 10 | 10 | 10 |
| Talc to | 100 | 100 | 100 | 100 | 100 | 100 |

EXAMPLE 25

The following example illustrates a lotion according to the invention which can be applied topically to the scalp to prevent hair loss and stimulate hair regrowth.

|  | % w/w |
|---|---|
| D-Glucaro-1,4-lactone | 7 |
| Minoxidil | 0.2 |
| ethanol | 16 |
| citric acid | 1.05 |
| water to | 100 |
| pH adjusted to 4.2 with sodium hydroxide | |

EXAMPLES 26 & 27

These examples illustrate hair tonics which are suitable for application to the hair and scalp.

The hair tonics had the following formulation:

|  | % w/w | |
|---|---|---|
|  | 26 | 27 |
| Hydroxamic acid* | 2 | — |
| Hydroxamic acid⁻ | — | 3 |
| ethanol | 50 | 50 |
| water | 48 | 47 |
| perfume | q.s. | q.s. |

*HONHCOCH$_2$CH(n-Pentyl)COLeu-PheNH$_2$
⁻HONHCOCH$_2$CH(n-Pentyl)COLeu-AlaNH$_2$

EXAMPLE 28

This example illustrates a microgel which is suitable for topical application to hair or scalp.

The gel had the following formulation:

|  |  | % w/w |
|---|---|---|
| A. | Polyoxyethylene (10) oleyl ether | 14.5 |
|  | Polyoxyethylene fatty glyceride | 14.5 |
|  | Light liquid petroleum | 13.7 |
|  | Propylene glycol | 7.6 |
|  | Sorbitol | 5.9 |
|  | Dilactone* | 4 |
| B. | Perfume | q.s. |
| C. | Water to | 100 |

*2,5-Di-O-acetyl-D-glucaro-1,4:6,3-dilactone

This microgel was prepared by heating part A to 90° C. and part C to 95° and then adding part C to part A with stirring. Part B was then added at 70° C. and the final mixture cooled and poured into jars at 55° C. to 60° C. On further cooling, a gel was formed.

EXAMPLES 29 to 31

These examples illustrate shampoos which are suitable for topical application to hair in order to cleanse it, at the same time delivering chemical inhibitors to the scalp to enhance hair growth or regrowth.

The shampoo had the following formulation:

|  | 29 | 30 | 31 |
|---|---|---|---|
| Triethanolamine lauryl sulphate | 16.8 | 18.0 | 16.8 |
| Coconut diethanolamide | 3.0 | — | 1.0 |
| Hydroxypropylmethyl-cellulose[1] | 0.25 | 0.1 | 0.3 |
| Corn syrup (80% solids)[2] | 20.5 | 40.0 | 21.0 |
| Dimethylpolysiloxane[3] | 1.0 | 1.0 | — |
| Volatile silicone[4] | — | — | 1.0 |
| Cationic cellulose[5] | 0.5 | — | 0.5 |
| Ethyl alcohol (SDA 40) | 9.0 | 10.0 | 10.0 |
| Vinyl carboxy polymer[7] | 0.75 | 0.3 | 0.75 |
| D-Galactosamine | 1 | — | — |
| Glucuronic acid propyl ester | — | 2 | — |
| Iduronic acid methyl ester | — | — | 5 |
| Perfume, colour, preservative | q.s. | q.s. | q.s. |
| Water to | 100 | 100 | 100 |
| Acid or base to pH: | 6.5 | 6.5 | 6.5 |

[1] Methocel E4M (Dow Chemical)
[2] 42 Dextrose equivalent (Staley 1300)
[3] 60,000 centistokes (Viscasil, GEC)
[4] Dow Corning 344
[5] Polymer JR 400
[6] Jaguar C-17
[7] Carbopol 941 (BF Goodrich)

EXAMPLES 32 to 35

The following formulations represent lotions which can be used topically in the treatment of bald or balding male or female heads.

| | % w/w | | | |
|---|---|---|---|---|
| | 32 | 33 | 34 | 35 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| N-Acetylmannosamine | 5 | — | — | — |
| Phosphorylated hesperidin | — | 1 | — | — |
| Sodium aurothiomalate | — | — | 2 | — |
| Substituted thiosemi-carbazone indoles | — | — | — | 4 |
| Perfume | 1 | 1 | 1 | 1 |
| Water to | 100 | 100 | 100 | 100 |

EXAMPLE 36

This Example also illustrates a lotion which is suitable for topical application to the scalp.

The lotion has the following formulation:

| | % w/w |
|---|---|
| Glucuronic acid | 1.5 |
| Diisopropyl sebacate | 10 |
| ethanol | 88.5 |
| perfume | q.s. |

EXAMPLE 37

This Example also illustrates a hair tonic which is suitable for application to hair or scalp.

The hair tonic has the following formulation:

| | % w/w |
|---|---|
| Glucurono-6,3-lactone | 0.2 |
| Pyroglutamic acid ethyl ester | 10 |
| ethanol | 40 |
| water | 49.80 |
| perfume | q.s. |

I claim:

1. A method for inducing, maintaining or increasing hair growth in a mammal which comprises: applying a hair growth inducing, maintaining or increasing amount of a composition to the skin or hair, said composition comprising:

(i) a first chemical inhibitor selected from the group consisting of:

(a) a direct proteoglycanase inhibitor selected from the group consisting of:
1,10-Phenanthroline
AcetylPhe-LeuSH
AcetylSer-LeuSH
AcetylTrp-LeuSH
AcetylPhe-Phe-LeuSH
$HSCH_2CH(\text{i-Butyl})COPheNH_2$
$HSCH_2CH(\text{i-Butyl})COLeu\text{-}PheNH_2$
AcetylTrp-IleSH
AcetylPhe-IleSH
$HOOCCH(\text{i-Butyl})Leu\text{-}Leu\text{-}LeuOCH_3$
$HOOCCH(\text{i-Butyl})Leu\text{-}Leu\text{-}AlaNH_2$
$HOOCCH(\text{i-Butyl})Leu\text{-}Leu\text{-}PheNH_2$
$HOOCCH(\text{i-Butyl})Leu\text{-}Leu\text{-}Leu\text{-}AlaNH_2$
$HONHCOCH_2CH(\text{n-Pentyl})COLeu\text{-}PheNH_2$
$HONHCOCH_2CH(\text{n-Pentyl})COLeu\text{-}AlaNH_2$
$HONHCOCH_2CH(\text{i-Butyl})COLeu\text{-}PheNH_2$
$HONHCOCH_2CH(\text{n-Pentyl})COVal\text{-}AlaNH_2$
and mixtures thereof;

(b) an indirect proteoglycanase inhibitor which is cationic oligomer;

(c) a glycosaminoglycanase inhibitor which is an at least one exoglycosidase inhibitor selected from the group consisting of aldonolactones and esterified aldonolactones of the formula:

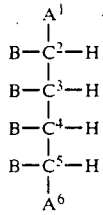

where
$A^1$ and $A^6$ are —H, —CH$_3$, [-C=0]

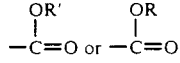

B is OR" or a lactone linkage to position 1 or 6, or —NHCOCH$_3$ and where R is —H or C$_2$ to C$_8$ alkyl, R' is the remainder of the molecule joined through another C atom at positions 2 to 5 to form a lactone, R" is —H or $C_2$ to $C_4$ acyl of either configuration with respect to the backbone of this molecule;

(d) a glycosaminoglycanase inhibitor which is an exoglycosidase inhibitor selected from the group consisting of monosaccharides and esterified monosaccharaides of the formula:

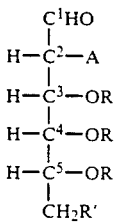

where
A is —OR or —NHCOCH$_3$,
R is —H, —SO$_3$M, $C_2$ to $C_4$ acyl,
R' is —H or —OR,
M is —H or a metal cation;

(e) a glycosaminoglycanase inhibitor which is an endoglycosidase inhibitor selected from the group consisting of:
phosphorylated hesperidin
sodium aurothiomalate
substituted thiosemicarbazone indoles, and
mixtures thereof;

(f) a glycosaminoglycanase inhibitor which is a sulphatase or sulphamatase inhibitor selected from water soluble salts having an anion selected from the group consisting of:
inorganic sulphate
sulphite
pyrophosphate
fluoride
borate
chloride
gluconate, and
mixtures thereof;

(g) a glycosaminoglycanase inhibitor which is the sulphatase inhibitor D-Glucosamine-3-sulphate; and (h) a glycosaminoglycan chain uptake inhibitor selected from the group consisting of hexuronic acids or esters thereof of the formula:

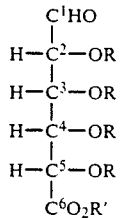

where
R is —H, —SO$_3$M, $C_2$ to $C_4$ acyl,
R' is —H or $C_2$ to $C_8$ alkyl; and (ii) a cosmetically acceptable vehicle for the chemical inhibitor; provided that when the first chemical inhibitor is a weak inhibitor, such that a 1mM aqueous solution of the inhibitor reduces proteoglycanase activity, glycosaminoglycan activity or cellular uptake of glycosaminoglycan chains, by from 5 to 50%, in accordance with at least one of the assay tests as herein described, then there is also present in the composition at least one of, a second chemical inhibitor selected from the group consisting of proteoglycanase inhibitors, glycosaminoglycanase inhibitors, glycosaminoglycan chain cellular uptake inhibitors or mixtures thereof, an activity enhancer; the total amount of chemical inhibitor present in the composition being sufficient to increase hair growth in a rat, when said composition is applied topically thereto, by at least 10% more than that obtainable using an equal amount of a control composition from which the said inhibitors have been omitted.

2. A method according to claim 1, in which the inhibitor is a cationic oligomer indirect proteoglycanase inhibitor selected from the group consisting of:
Arq-Arq-Arq,
Cys-Arq-Arq-Arq-Lys-Arq-Arq,
Pro-Arq-Arq-Arq-Arq,
Arq-Pro-Val-Arq-Arq-Arq-Arq-Arq-Pro-Val, and mixtures thereof.

3. A method according to claim 1 wherein the inhibitor is an aldonolactone exoglycosidase inhibitor selected from the group consisting of:
L-Galactonic acid-lactone
L-Arabino-1, 5-lactone
D-Fucono-1, 5-lactone
D-Glucaro-1, 4-lacone
D-Glucurono-6, 3-lactone
Galactaric acid lactone
2-Acetamido-2-deoxygluconolactone
2-Acetamido-2-deoxygalactonolactone
D-Glucaro-1,4:6,3-dilactone
L-Idaro-1,4-lactone, and
mixture thereof.

4. A method according to claim 1 in which the inhibitor is an exoglycosidase inhibitor which is an esterified aldonolactone selected from the group consisting of:
2, 3, 5, -Tri-O-acetyl-D-glucaro-1,4-lactone, 2,5-Di-o-acetyl-D-glucaro-1, 4:6, 3-dilactone and mixtures thereof.

5. A method according to claim 1 in which the inhibitor is a monosaccharide or esterified monosaccharide exoglycosidase inhibitor selected from the group consisting of:
N-Acetylglycosamine,
N-Acetylgalactosamine,
D-Galactosamine, and
mixtures thereof.

6. A method according to claim 1 in which the inhibitor is a sulphatase inhibitor selected from the group consisting of the anions:
inorganic sulphate,
sulphite,
pyrophosphate,
fluoride
borate
chloride
gluconate, and mixtures thereof,
each anion being in the form of a water-soluble metal or ammonium salt.

7. A method according to claim 6 in which the salt is selected from the group consisting of magnesium sulphate and zinc gluconate.

8. A method according to claim 7, in which the salt is magnesium sulphate.

9. A method according to claim 6 in which the sulphamase inhibitor is selected from the group consisting of the anions:

inorganic sulphate
sulphite
pyrophosphate
fluoride
borate, and
   mixtures thereof,
each anion being in the form of a water-soluble metal or ammonia salt.

10. A method according to claim 1, in which the inhibitor is a hexuronic acid glycosaminoglycan chain uptake inhibitor selected from the group consisting of glucuronic acid, iduronic acid and mixtures thereof.

11. A method according to claim 1, in which the total amount of chemical inhibitor is sufficient to increase hair growth in a rat, when the composition is applied topically thereto, by 20% to 50% more than that obtainable using the same amount of a control composition from which said inhibitors have been omitted.

12. A method according to claim 1, in which the total amount of chemical inhibitor in the composition, is sufficient to increase their growth in a rat, when said composition is applied topically thereto, by at least 50% more than that obtained using the same amount of a control composition from which said inhibitors have been omitted.

13. A method according to claim 1, in which the amount of the chemical inhibitor in the composition comprises from 0.0001 to 99% by weight of the composition.

14. A method according to claim 13, in which the amount of chemical inhibitor comprises from 0.1 to 20% by weight of the composition.

15. A method according to claim 1 in which the composition additionally comprises from 0.01 to 10% by weight of a perfume.

16. A method according to claim 1 in which the composition additionally comprises an activity enhancer.

17. A method according to claim 16, in which the activity enhancer comprises at least one hair growth stimulant selected from the group consisting of:
Benzalkonium chloride
Benzethonium chloride
Phenol
Estradiol
Diphenhydramine hydrocholoride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Panthenol
Castor oil
Hinokitiol
Prednisolone
Resorcinol, and
mixtures thereof.

18. A method according to claim 16, in which the activity enhancer is a hair growth stimulant selected from the group consisting of α-1,4 esterified dissaccharides of the formula:

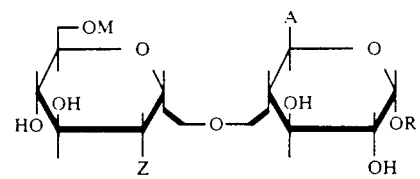

where
Z represents a functional nitrogen group selected from an azide group or a group having the structure -NHB, in which B represents —H an acetyl group or sulphate as a salt with an organic or inorganic cation; M represents —H or $SO_3m_1$, or acetyl group, and $M_1$ is an organic or metallic cation, or an acetyl group, and;
R represents a $C_1$ to $C_4$ alkyl radical, or an aryl radical;
A represents a functional group selected from a carboxylic acid group of —$COOR_1$, where $R_1$ represents —H a $C_1$ to $C_4$ alkyl radical or a metal.

19. A method according to claim 16, in which the activity enhancer is a hair growth stimulant selected from the group consisting of esterified oligosaccharides, including at least one esterified disaccharide unit consisting of a uronic acid residue of the formula:

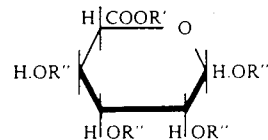

and a hexosamine residue of the formula:

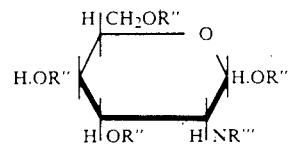

where
R' is —H, $C_3$ to $C_{10}$ alkyl or

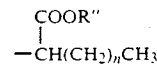

R'' is —H, $C_1$ to $C_4$ alkyl, —$CO(CH_2)_mCH_3$, —$SO_3M$,
R''' is —H, —$CO(CH_2)_mCH_3$, or —$SO_3M$,
M is —H, or a metallic or organic cation
n is 0 or an integer of from 1 to 7, and
m is 0 or the integer 1 or 2;
the groups designated R'' being the same or different, one R'' group from each pyranose ring structure being linked by a glycosidic linkage having the configuration α-1,3, α-1,4, β-1,3 or β-1,4; and the —COOR', —$CH_2OR''$ and —OR'' groups being of either configuration with respect to the pyranose rings.

20. A method according to claim 16, in which the activity enhancer is a hair growth stimulant selected from the group consisting of:
minoxidil glucuronides,
minoxidil sulphates, and mixtures thereof.

21. A method according to claim 16, in which the activity enhancer is a penetration enhancer.

22. A method according to claim 21, which the penetration enhancer is selected from the group consisting of:
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Debenzyl sebacate
Dibutyl phthalate
Dibutyl acelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl Laurate
Ethyl caprate
Ethyl caprylate
Butyl stearate
Benzyl salicylate
2-hydroxypropanoic acid
2-hydroxyoctanoic acid, and mixtures thereof.

23. A method according to claim 21, in which the penetration enhancer is selected from the group consisting of esters of pyroglutamic acid having the structure:

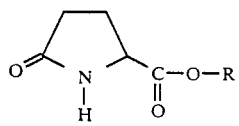  (1)

where R is $C_1$ to $C_{30}$ alkyl, or

and where R' and R" are the same or different and are each represented by H or the grouping:

[$(CH_3)_u$, $(CH_2OH)_v$, $(CH_2)_w$, $(CH_3CH_2)_x$, 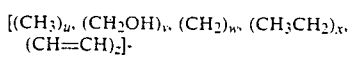]-  (2)

where
u is zero or 1
v is zero, or the integer 1 or 2,
w is zero, or an integer of from 1 to 21
x is zero, or an integer of from 1 to 4,
y is zero, or the integer 1 or 2,
z is zero, or an integer of from 1 to 22, and
u+v+w+x+y+z is an integer of from 1 to 22;
provided that when the subgrouping (CH+CH) is present, then the total number of carbon atoms in said grouping is from 10 to 22.

24. A method according to claim 23, in which the ester of pyroglutamic acid is selected from the group consisting of:
pyroglutamic acid methyl ester
pyroglutamic acid ethyl ester
pyroglutamic acid n-propyl ester
pyroglutamic acid n-butyl ester
pyroglutamic acid n-heptyl ester
pyroglutamic acid n-octyl ester
pyroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradcyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester, and mixtures thereof.

25. A method according to claim 23, in which the ester of pyroglutamic acid is selected from the group consisting of:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-1-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate)
glyceryl di(2-[pyroglutamoyloxy]-n-propionate), and mixtures thereof.

26. A method according to claim 21, in which the penetration enhancer is selected from the group consisting of:
Dimethyl sulphoxide N,N-Dimethyl acetamide
N,N-Dimethyl formamide
2-Pyrrolidonel-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide
1-Dodecylazacyloheptan-2-one, and mixtures thereof.

27. A method according to claim 21, in which the penetration enhancer comprises an anionic surface active agent selected from the group consisting of:
metallic or alkanolamine salts of fatty acids
alkyl benzene sulfonates
alkyl sulphates
alkyl ether sulphates
sulphosuccinates
monoglyceride sulphates
isethionates
methyl taurides
acyl sarcosinates
acyl peptides
acyl lactylates
polyalkoxylated ether glycollates
phosphates, and mixtures thereof.

28. A method according to claim 21, in which the penetration enhancer comprises an amphoteric surface active agent selected from the group consisting of:
imidazol compounds
N-alkylamino acids
betaines, and
mixtures thereof 29. A method according to claim 21, in which the penetration enhancer comprises a nonionic surface active agent selected from the group consisting of:
fatty acid alkanolamides
esters of polyalcohols
polyglycerol esters
polyalkoxylated compounds
ethers
ester ethers
amine oxides, and
mixtures thereof.

30. A method of claim 1 wherein the composition is in the form of a lotion, cream, shampoo or hair conditioner.

31. A method of claim 1 wherein the mammal is a human being.

* * * * *